United States Patent
Holecek et al.

(10) Patent No.: US 8,696,743 B2
(45) Date of Patent: Apr. 15, 2014

(54) TISSUE ATTACHMENT DEVICES AND METHODS FOR PROSTHETIC HEART VALVES

(75) Inventors: Arin N. Holecek, Liberty Lake, WA (US); Carolyn Majkrzak, San Clemente, CA (US); Carol E. Eberhardt, Fullerton, CA (US); Billie J. Millwee, Fullerton, CA (US); Thao M. Nguyen, Cypress, CA (US); Janice L. Shay, Lake Forest, CA (US); Cynthia H. Chiu, Tustin, CA (US); Tara S. Kupumbati, Irvine, CA (US)

(73) Assignee: Medtronic, Inc., Minneapolis, MN (US)

( * ) Notice: Subject to any disclaimer, the term of this patent is extended or adjusted under 35 U.S.C. 154(b) by 631 days.

(21) Appl. No.: 12/424,768

(22) Filed: Apr. 16, 2009

(65) Prior Publication Data
US 2010/0023120 A1    Jan. 28, 2010

Related U.S. Application Data

(60) Provisional application No. 61/125,203, filed on Apr. 23, 2008.

(51) Int. Cl.
*A61F 2/24* (2006.01)

(52) U.S. Cl.
USPC ........ 623/2.12; 623/1.24; 623/1.26; 623/2.17

(58) Field of Classification Search
USPC .................. 623/2.17–2.19, 1.24, 1.26, 2.1
See application file for complete search history.

(56) References Cited

U.S. PATENT DOCUMENTS

| | | | |
|---|---|---|---|
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 3,868,956 | A | 3/1975 | Alfidi et al. |
| 4,035,849 | A | 7/1977 | Angell et al. |

(Continued)

FOREIGN PATENT DOCUMENTS

| | | |
|---|---|---|
| CN | 2007-100074433 | 8/2007 |
| DE | 195 32 846 | 3/1997 |

(Continued)

OTHER PUBLICATIONS

U.S. Appl. No. 12/476,702, filed Jun. 2, 2009.

(Continued)

*Primary Examiner* — Thomas J Sweet
*Assistant Examiner* — Seema Mathew

(57) ABSTRACT

A multi-leaflet valve, which includes at least two leaflets, an outer tube, and a seam protector for each seam. Each seam protector is positioned to be in contact with a portion of the outer tube, with tube portions and leaflet ends being positioned between adjacent seam protection pieces. The seam protectors provide a lower stress surface about which the leaflets can bend or flex during their opening and closing. The seam protectors may include an enlarged end portion with an extending straight surface, an inverted U-shaped structure, or a sinusoidal-shaped structure, for example. The valve can further be provided with a seam cover or protector that is stitched onto the seam allowance of the layers of one or more of the seams. The seams can be provided with one or more inserts to fill spaces between adjacent tissue layers and create tension in certain material sheets.

16 Claims, 9 Drawing Sheets

(56) References Cited

U.S. PATENT DOCUMENTS

| | | | |
|---|---|---|---|
| 4,056,854 A | 11/1977 | Boretos et al. | |
| 4,106,129 A | 8/1978 | Carpentier et al. | |
| 4,192,020 A * | 3/1980 | Davis et al. | 623/2.19 |
| 4,222,126 A | 9/1980 | Boretos et al. | |
| 4,265,694 A | 5/1981 | Boretos | |
| 4,297,749 A | 11/1981 | Davis et al. | |
| 4,343,048 A | 8/1982 | Ross et al. | |
| 4,345,340 A | 8/1982 | Rosen | |
| 4,388,735 A * | 6/1983 | Ionescu et al. | 623/2.19 |
| 4,425,908 A | 1/1984 | Simon | |
| 4,441,216 A * | 4/1984 | Ionescu et al. | 623/2.19 |
| 4,470,157 A | 9/1984 | Love | |
| 4,501,030 A * | 2/1985 | Lane | 623/2.18 |
| 4,574,803 A | 3/1986 | Storz | |
| 4,580,568 A | 4/1986 | Gianturco | |
| 4,592,340 A | 6/1986 | Boyles | |
| 4,610,688 A | 9/1986 | Silvestrini et al. | |
| 4,647,283 A | 3/1987 | Carpentier et al. | |
| 4,648,881 A | 3/1987 | Carpentier et al. | |
| 4,665,906 A | 5/1987 | Jervis | |
| 4,681,908 A | 7/1987 | Broderick et al. | |
| 4,710,192 A | 12/1987 | Liotta et al. | |
| 4,787,899 A | 11/1988 | Lazarus | |
| 4,787,901 A | 11/1988 | Baykut | |
| 4,796,629 A | 1/1989 | Grayzel | |
| 4,819,751 A | 4/1989 | Shimada et al. | |
| 4,834,755 A | 5/1989 | Silvestrini et al. | |
| 4,856,516 A | 8/1989 | Hillstead | |
| 4,872,874 A | 10/1989 | Taheri | |
| 4,878,495 A | 11/1989 | Grayzel | |
| 4,878,906 A | 11/1989 | Lindemann et al. | |
| 4,883,458 A | 11/1989 | Shiber | |
| 4,909,252 A | 3/1990 | Goldberger | |
| 4,917,102 A | 4/1990 | Miller et al. | |
| 4,922,905 A | 5/1990 | Strecker | |
| 4,994,077 A | 2/1991 | Dobben | |
| 5,002,559 A | 3/1991 | Tower | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,085,635 A | 2/1992 | Cragg | |
| 5,089,015 A | 2/1992 | Ross | |
| 5,152,771 A | 10/1992 | Sabbaghian et al. | |
| 5,161,547 A | 11/1992 | Tower | |
| 5,163,953 A | 11/1992 | Vince | |
| 5,167,628 A | 12/1992 | Boyles | |
| 5,217,483 A | 6/1993 | Tower | |
| 5,232,445 A | 8/1993 | Bonzel | |
| 5,272,909 A | 12/1993 | Nguyen et al. | |
| 5,295,958 A | 3/1994 | Shturman | |
| 5,327,774 A | 7/1994 | Nguyen et al. | |
| 5,332,402 A | 7/1994 | Teitelbaum | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A | 5/1995 | Andersen et al. | |
| 5,415,633 A | 5/1995 | Lazarus et al. | |
| 5,431,676 A | 7/1995 | Dubrul et al. | |
| 5,443,446 A | 8/1995 | Shturman | |
| 5,480,424 A | 1/1996 | Cox | |
| 5,489,294 A | 2/1996 | McVenes et al. | |
| 5,489,297 A | 2/1996 | Duran | |
| 5,496,346 A | 3/1996 | Horzewski et al. | |
| 5,500,014 A | 3/1996 | Quijano et al. | |
| 5,507,767 A | 4/1996 | Maeda et al. | |
| 5,545,209 A | 8/1996 | Roberts et al. | |
| 5,545,211 A | 8/1996 | An et al. | |
| 5,545,214 A | 8/1996 | Stevens | |
| 5,554,185 A | 9/1996 | Block et al. | |
| 5,575,818 A | 11/1996 | Pinchuk | |
| 5,580,922 A | 12/1996 | Park et al. | |
| 5,591,195 A | 1/1997 | Taheri et al. | |
| 5,609,626 A | 3/1997 | Quijano et al. | |
| 5,645,559 A | 7/1997 | Hachtman et al. | |
| 5,667,523 A | 9/1997 | Bynon et al. | |
| 5,674,277 A | 10/1997 | Freitag | |
| 5,702,368 A | 12/1997 | Stevens et al. | |
| 5,713,953 A | 2/1998 | Vallana et al. | |
| 5,716,417 A | 2/1998 | Girard et al. | |
| 5,746,709 A | 5/1998 | Rom et al. | |
| 5,749,890 A | 5/1998 | Shaknovich | |
| 5,766,151 A | 6/1998 | Valley et al. | |
| 5,782,809 A | 7/1998 | Umeno et al. | |
| 5,800,456 A | 9/1998 | Maeda et al. | |
| 5,800,508 A | 9/1998 | Goicoechea et al. | |
| 5,817,126 A | 10/1998 | Imran | |
| 5,824,041 A | 10/1998 | Lenker | |
| 5,824,043 A | 10/1998 | Cottone, Jr. | |
| 5,824,053 A | 10/1998 | Khosravi et al. | |
| 5,824,056 A | 10/1998 | Rosenberg | |
| 5,824,061 A | 10/1998 | Quijano et al. | |
| 5,824,064 A | 10/1998 | Taheri | |
| 5,855,597 A | 1/1999 | Jayaraman | |
| 5,855,601 A | 1/1999 | Bessler et al. | |
| 5,860,966 A | 1/1999 | Tower | |
| 5,861,028 A | 1/1999 | Angell | |
| 5,868,783 A | 2/1999 | Tower | |
| 5,891,191 A | 4/1999 | Stinson | |
| 5,895,419 A * | 4/1999 | Tweden et al. | 623/2.36 |
| 5,906,619 A | 5/1999 | Olson et al. | |
| 5,913,842 A | 6/1999 | Boyd et al. | |
| 5,925,063 A | 7/1999 | Khosravi | |
| 5,957,949 A | 9/1999 | Leonhardt et al. | |
| 5,968,068 A | 10/1999 | Dehdashtian et al. | |
| 5,984,957 A | 11/1999 | Laptewicz, Jr. et al. | |
| 5,997,573 A | 12/1999 | Quijano et al. | |
| 6,022,370 A | 2/2000 | Tower | |
| 6,027,525 A | 2/2000 | Suh et al. | |
| 6,029,671 A | 2/2000 | Stevens et al. | |
| 6,042,589 A | 3/2000 | Marianne | |
| 6,042,598 A | 3/2000 | Tsugita et al. | |
| 6,042,607 A | 3/2000 | Williamson, IV | |
| 6,051,014 A | 4/2000 | Jang | |
| 6,059,809 A | 5/2000 | Amor et al. | |
| 6,110,201 A | 8/2000 | Quijano et al. | |
| 6,146,366 A | 11/2000 | Schachar | |
| 6,159,239 A | 12/2000 | Greenhalgh | |
| 6,162,245 A | 12/2000 | Jayaraman | |
| 6,171,335 B1 | 1/2001 | Wheatley et al. | |
| 6,200,336 B1 | 3/2001 | Pavcnik et al. | |
| 6,203,550 B1 | 3/2001 | Olson | |
| 6,210,408 B1 | 4/2001 | Chandrasekaran et al. | |
| 6,218,662 B1 | 4/2001 | Tchakarov et al. | |
| 6,221,006 B1 | 4/2001 | Dubrul et al. | |
| 6,221,091 B1 | 4/2001 | Khosravi | |
| 6,245,102 B1 | 6/2001 | Jayaraman | |
| 6,248,116 B1 | 6/2001 | Chevilon | |
| 6,258,114 B1 | 7/2001 | Konya et al. | |
| 6,258,115 B1 | 7/2001 | Dubrul | |
| 6,258,120 B1 | 7/2001 | McKenzie et al. | |
| 6,277,555 B1 | 8/2001 | Duran et al. | |
| 6,299,637 B1 | 10/2001 | Shaolia et al. | |
| 6,302,906 B1 | 10/2001 | Goicoechea et al. | |
| 6,309,382 B1 | 10/2001 | Garrison et al. | |
| 6,309,417 B1 | 10/2001 | Spence et al. | |
| 6,338,735 B1 | 1/2002 | Stevens | |
| 6,348,063 B1 | 2/2002 | Yassour et al. | |
| 6,350,277 B1 | 2/2002 | Kocur | |
| 6,352,708 B1 | 3/2002 | Duran et al. | |
| 6,371,970 B1 | 4/2002 | Khosravi et al. | |
| 6,371,983 B1 | 4/2002 | Lane | |
| 6,380,457 B1 | 4/2002 | Yurek et al. | |
| 6,398,807 B1 | 6/2002 | Chouinard et al. | |
| 6,409,750 B1 | 6/2002 | Hyodoh et al. | |
| 6,425,916 B1 | 7/2002 | Garrison et al. | |
| 6,440,164 B1 | 8/2002 | DiMatteo et al. | |
| 6,454,799 B1 * | 9/2002 | Schreck | 623/2.18 |
| 6,458,153 B1 | 10/2002 | Bailey et al. | |
| 6,461,382 B1 | 10/2002 | Cao | |
| 6,475,239 B1 | 11/2002 | Campbell et al. | |
| 6,482,228 B1 | 11/2002 | Norred | |

(56) References Cited

U.S. PATENT DOCUMENTS

| | | | |
|---|---|---|---|
| 6,488,704 B1 | 12/2002 | Connelly et al. | |
| 6,494,909 B2 | 12/2002 | Greenhalgh | |
| 6,503,272 B2 | 1/2003 | Duerig et al. | |
| 6,508,833 B2 | 1/2003 | Pavcnik et al. | |
| 6,527,800 B1 | 3/2003 | McGuckin, Jr. et al. | |
| 6,530,949 B2 | 3/2003 | Konya et al. | |
| 6,530,952 B2 | 3/2003 | Vesely | |
| 6,562,031 B2 | 5/2003 | Chandrasekaran et al. | |
| 6,562,058 B2 | 5/2003 | Seguin et al. | |
| 6,569,196 B1 | 5/2003 | Vesely | |
| 6,585,758 B1 | 7/2003 | Chouinard et al. | |
| 6,592,546 B1 | 7/2003 | Barbut et al. | |
| 6,605,112 B1 | 8/2003 | Moll et al. | |
| 6,613,077 B2 | 9/2003 | Gilligan et al. | |
| 6,622,604 B1 | 9/2003 | Chouinard et al. | |
| 6,635,068 B1 | 10/2003 | Dubrul et al. | |
| 6,652,571 B1 | 11/2003 | White et al. | |
| 6,652,578 B2 | 11/2003 | Bailey et al. | |
| 6,656,213 B2 | 12/2003 | Solem | |
| 6,673,109 B2 | 1/2004 | Cox | |
| 6,676,698 B2 | 1/2004 | McGuckin, Jr. et al. | |
| 6,682,558 B2 | 1/2004 | Tu et al. | |
| 6,682,559 B2 | 1/2004 | Myers et al. | |
| 6,685,739 B2 | 2/2004 | DiMatteo et al. | |
| 6,689,144 B2 | 2/2004 | Gerberding | |
| 6,689,164 B1 | 2/2004 | Seguin | |
| 6,692,512 B2 | 2/2004 | Jang | |
| 6,692,513 B2 | 2/2004 | Streeter et al. | |
| 6,695,878 B2 | 2/2004 | McGuckin, Jr. et al. | |
| 6,702,851 B1 | 3/2004 | Chinn et al. | |
| 6,719,789 B2 | 4/2004 | Cox | |
| 6,730,118 B2 | 5/2004 | Spenser et al. | |
| 6,730,377 B2 | 5/2004 | Wang | |
| 6,733,525 B2 | 5/2004 | Yang et al. | |
| 6,736,846 B2 | 5/2004 | Cox | |
| 6,752,828 B2 | 6/2004 | Thornton | |
| 6,769,434 B2 | 8/2004 | Liddicoat et al. | |
| 6,786,925 B1 | 9/2004 | Schoon | |
| 6,790,229 B1 | 9/2004 | Berreklouw | |
| 6,792,979 B2 | 9/2004 | Konya et al. | |
| 6,797,002 B2 | 9/2004 | Spence | |
| 6,821,297 B2 | 11/2004 | Snyders | |
| 6,830,575 B2 | 12/2004 | Stenzel et al. | |
| 6,830,584 B1 | 12/2004 | Seguin | |
| 6,830,585 B1 | 12/2004 | Artof | |
| 6,846,325 B2 | 1/2005 | Liddicoat | |
| 6,866,650 B2 | 3/2005 | Stevens | |
| 6,872,223 B2 | 3/2005 | Roberts | |
| 6,875,231 B2 | 4/2005 | Anduiza et al. | |
| 6,883,522 B2 | 4/2005 | Spence et al. | |
| 6,887,266 B2 | 5/2005 | Williams et al. | |
| 6,890,330 B2 | 5/2005 | Streeter et al. | |
| 6,893,460 B2 | 5/2005 | Spenser et al. | |
| 6,896,690 B1 | 5/2005 | Lambrecht et al. | |
| 6,908,481 B2 | 6/2005 | Cribier | |
| 6,913,600 B2 | 7/2005 | Valley et al. | |
| 6,929,653 B2 | 8/2005 | Streeter | |
| 6,939,365 B1 | 9/2005 | Fogarty et al. | |
| 6,951,571 B1 | 10/2005 | Srivastava | |
| 6,986,742 B2 | 1/2006 | Hart et al. | |
| 6,989,027 B2 | 1/2006 | Allen et al. | |
| 6,989,028 B2 | 1/2006 | Lashinski et al. | |
| 6,991,649 B2 | 1/2006 | Sievers | |
| 7,018,401 B1 | 3/2006 | Hyodoh et al. | |
| 7,041,128 B2 | 5/2006 | McGuckin, Jr. et al. | |
| 7,044,966 B2 | 5/2006 | Svanidze et al. | |
| 7,048,014 B2 | 5/2006 | Hyodoh et al. | |
| 7,097,659 B2 | 8/2006 | Woolfson et al. | |
| 7,101,396 B2 | 9/2006 | Artof et al. | |
| 7,105,016 B2 | 9/2006 | Shui et al. | |
| 7,115,141 B2 | 10/2006 | Menz et al. | |
| 7,147,663 B1 | 12/2006 | Berg et al. | |
| 7,153,324 B2 | 12/2006 | Case et al. | |
| 7,160,319 B2 | 1/2007 | Chouinard et al. | |
| 7,175,656 B2 | 2/2007 | Khairkhahan | |
| 7,186,265 B2 | 3/2007 | Sharkawy et al. | |
| 7,195,641 B2 | 3/2007 | Palmaz et al. | |
| 7,198,646 B2 | 4/2007 | Figulla et al. | |
| 7,201,761 B2 | 4/2007 | Woolfson et al. | |
| 7,201,772 B2 | 4/2007 | Schwammenthal et al. | |
| 7,252,682 B2 | 8/2007 | Seguin | |
| 7,300,457 B2 | 11/2007 | Palmaz | |
| 7,300,463 B2 | 11/2007 | Liddicoat | |
| 7,316,706 B2 | 1/2008 | Bloom et al. | |
| 7,329,278 B2 | 2/2008 | Seguin | |
| 7,335,218 B2 | 2/2008 | Wilson et al. | |
| 7,338,520 B2 | 3/2008 | Bailey et al. | |
| 7,374,571 B2 | 5/2008 | Pease et al. | |
| 7,381,218 B2 | 6/2008 | Schreck | |
| 7,384,411 B1 | 6/2008 | Condado | |
| 7,429,269 B2 | 9/2008 | Schwammenthal et al. | |
| 7,442,204 B2 | 10/2008 | Schwammenthal et al. | |
| 7,462,191 B2 | 12/2008 | Spenser et al. | |
| 7,470,284 B2 | 12/2008 | Lambrecht et al. | |
| 7,473,275 B2* | 1/2009 | Marquez | 623/2.38 |
| 7,481,838 B2 | 1/2009 | Carpentier et al. | |
| 7,544,206 B2 | 6/2009 | Cohn et al. | |
| 7,556,646 B2 | 7/2009 | Yang et al. | |
| 7,628,805 B2* | 12/2009 | Spenser et al. | 623/1.24 |
| 7,758,640 B2* | 7/2010 | Vesely | 623/2.38 |
| 8,052,750 B2* | 11/2011 | Tuval et al. | 623/2.17 |
| 8,500,798 B2* | 8/2013 | Rowe et al. | 623/2.1 |
| 8,568,475 B2* | 10/2013 | Nguyen et al. | 623/2.12 |
| 2001/0001314 A1 | 5/2001 | Davison et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0011189 A1 | 8/2001 | Drasler et al. | |
| 2001/0021872 A1 | 9/2001 | Bailey et al. | |
| 2001/0025196 A1 | 9/2001 | Chinn et al. | |
| 2001/0032013 A1 | 10/2001 | Marton | |
| 2001/0039450 A1 | 11/2001 | Pavcnik et al. | |
| 2001/0041928 A1 | 11/2001 | Pavcnik et al. | |
| 2001/0044647 A1 | 11/2001 | Pinchuk et al. | |
| 2002/0010508 A1 | 1/2002 | Chobotov | |
| 2002/0029014 A1 | 3/2002 | Jayaraman | |
| 2002/0032480 A1 | 3/2002 | Spence et al. | |
| 2002/0032481 A1 | 3/2002 | Gabbay | |
| 2002/0035396 A1 | 3/2002 | Heath | |
| 2002/0042650 A1 | 4/2002 | Vardi et al. | |
| 2002/0052651 A1* | 5/2002 | Myers et al. | 623/2.15 |
| 2002/0058995 A1 | 5/2002 | Stevens | |
| 2002/0072789 A1 | 6/2002 | Hackett et al. | |
| 2002/0099439 A1 | 7/2002 | Schwartz et al. | |
| 2002/0103533 A1 | 8/2002 | Langberg et al. | |
| 2002/0107565 A1 | 8/2002 | Greenhalgh | |
| 2002/0111674 A1 | 8/2002 | Chouinard et al. | |
| 2002/0123802 A1 | 9/2002 | Snyders | |
| 2002/0133183 A1 | 9/2002 | Lentz et al. | |
| 2002/0133226 A1* | 9/2002 | Marquez et al. | 623/2.11 |
| 2002/0138138 A1 | 9/2002 | Yang | |
| 2002/0151970 A1 | 10/2002 | Garrison et al. | |
| 2002/0161392 A1 | 10/2002 | Dubrul | |
| 2002/0161394 A1 | 10/2002 | Macoviak et al. | |
| 2002/0193871 A1 | 12/2002 | Beyersdorf et al. | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0028247 A1 | 2/2003 | Cali | |
| 2003/0036791 A1 | 2/2003 | Philipp et al. | |
| 2003/0040772 A1 | 2/2003 | Hyodoh et al. | |
| 2003/0040792 A1 | 2/2003 | Gabbay | |
| 2003/0050694 A1 | 3/2003 | Yang et al. | |
| 2003/0055495 A1 | 3/2003 | Pease et al. | |
| 2003/0065386 A1 | 4/2003 | Weadock | |
| 2003/0109924 A1 | 6/2003 | Cribier | |
| 2003/0125795 A1 | 7/2003 | Pavcnik et al. | |
| 2003/0130726 A1 | 7/2003 | Thorpe et al. | |
| 2003/0130729 A1 | 7/2003 | Paniagua et al. | |
| 2003/0139804 A1 | 7/2003 | Hankh et al. | |
| 2003/0149475 A1 | 8/2003 | Hyodoh et al. | |
| 2003/0149476 A1 | 8/2003 | Damm et al. | |

(56) References Cited

U.S. PATENT DOCUMENTS

| | | |
|---|---|---|
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2004/0034411 A1 | 2/2004 | Quijano et al. |
| 2004/0039436 A1* | 2/2004 | Spenser et al. ............... 623/1.13 |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Sequin et al. |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen et al. |
| 2004/0254636 A1 | 12/2004 | Flagle et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0096739 A1* | 5/2005 | Cao ............... 623/2.19 |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0217802 A1* | 9/2006 | Ruiz et al. ............ 623/2.11 |
| 2006/0229719 A1* | 10/2006 | Marquez et al. ............ 623/2.41 |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0016288 A1* | 1/2007 | Gurskis et al. ............ 623/2.11 |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Jantz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0208550 A1* | 9/2007 | Cao et al. ............ 703/11 |
| 2007/0225681 A1 | 9/2007 | House |
| 2007/0232898 A1 | 10/2007 | Huynh et al. |

(56) References Cited

U.S. PATENT DOCUMENTS

| | | | |
|---|---|---|---|
| 2007/0233228 A1* | 10/2007 | Eberhardt et al. | 623/1.13 |
| 2007/0233237 A1 | 10/2007 | Krivoruchko | |
| 2007/0233238 A1 | 10/2007 | Huynh et al. | |
| 2007/0238979 A1 | 10/2007 | Huynh et al. | |
| 2007/0239254 A1 | 10/2007 | Marchand et al. | |
| 2007/0239265 A1 | 10/2007 | Birdsall | |
| 2007/0239266 A1 | 10/2007 | Birdsall | |
| 2007/0239269 A1 | 10/2007 | Dolan et al. | |
| 2007/0239273 A1 | 10/2007 | Allen | |
| 2007/0244544 A1 | 10/2007 | Birdsall et al. | |
| 2007/0244545 A1 | 10/2007 | Birdsall et al. | |
| 2007/0244546 A1 | 10/2007 | Francis | |
| 2007/0244553 A1 | 10/2007 | Rafiee et al. | |
| 2007/0244554 A1 | 10/2007 | Rafiee et al. | |
| 2007/0244555 A1 | 10/2007 | Rafiee et al. | |
| 2007/0244556 A1 | 10/2007 | Rafiee et al. | |
| 2007/0244557 A1 | 10/2007 | Rafiee et al. | |
| 2007/0250160 A1 | 10/2007 | Rafiee | |
| 2007/0255394 A1 | 11/2007 | Ryan | |
| 2007/0255396 A1 | 11/2007 | Douk et al. | |
| 2007/0288000 A1 | 12/2007 | Bonan | |
| 2008/0004688 A1 | 1/2008 | Spenser et al. | |
| 2008/0004696 A1 | 1/2008 | Vesely | |
| 2008/0009940 A1 | 1/2008 | Cribier | |
| 2008/0015671 A1 | 1/2008 | Bonhoeffer | |
| 2008/0021552 A1 | 1/2008 | Gabbay | |
| 2008/0048656 A1 | 2/2008 | Tan | |
| 2008/0065011 A1 | 3/2008 | Marchand et al. | |
| 2008/0065206 A1 | 3/2008 | Liddicoat | |
| 2008/0071361 A1 | 3/2008 | Tuval et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0071368 A1 | 3/2008 | Tuval et al. | |
| 2008/0077234 A1 | 3/2008 | Styrc | |
| 2008/0082165 A1 | 4/2008 | Wilson et al. | |
| 2008/0082166 A1 | 4/2008 | Styrc et al. | |
| 2008/0133003 A1 | 6/2008 | Seguin et al. | |
| 2008/0140189 A1 | 6/2008 | Nguyen et al. | |
| 2008/0147105 A1 | 6/2008 | Wilson et al. | |
| 2008/0147180 A1 | 6/2008 | Ghione et al. | |
| 2008/0147181 A1 | 6/2008 | Ghione et al. | |
| 2008/0147182 A1 | 6/2008 | Righini et al. | |
| 2008/0154356 A1 | 6/2008 | Obermiller et al. | |
| 2008/0161910 A1 | 7/2008 | Revuelta et al. | |
| 2008/0161911 A1 | 7/2008 | Revuelta et al. | |
| 2008/0183273 A1 | 7/2008 | Mesana et al. | |
| 2008/0188928 A1 | 8/2008 | Salahieh et al. | |
| 2008/0215143 A1 | 9/2008 | Seguin et al. | |
| 2008/0215144 A1 | 9/2008 | Ryan et al. | |
| 2008/0228254 A1 | 9/2008 | Ryan | |
| 2008/0228263 A1 | 9/2008 | Ryan | |
| 2008/0234797 A1 | 9/2008 | Styrc | |
| 2008/0243246 A1 | 10/2008 | Ryan et al. | |
| 2008/0255651 A1 | 10/2008 | Dwork | |
| 2008/0255660 A1 | 10/2008 | Guyenot et al. | |
| 2008/0255661 A1 | 10/2008 | Straubinger et al. | |
| 2008/0262593 A1 | 10/2008 | Ryan et al. | |
| 2009/0005863 A1 | 1/2009 | Goetz et al. | |
| 2009/0012600 A1 | 1/2009 | Styrc et al. | |
| 2009/0048656 A1 | 2/2009 | Wen | |
| 2009/0054976 A1 | 2/2009 | Tuval et al. | |
| 2009/0069886 A1 | 3/2009 | Suri et al. | |
| 2009/0069887 A1 | 3/2009 | Righini et al. | |
| 2009/0069889 A1 | 3/2009 | Suri et al. | |
| 2009/0138079 A1 | 5/2009 | Tuval et al. | |
| 2009/0164004 A1 | 6/2009 | Cohn | |
| 2009/0171447 A1 | 7/2009 | VonSegesser et al. | |
| 2009/0192585 A1 | 7/2009 | Bloom et al. | |
| 2009/0192586 A1 | 7/2009 | Tabor et al. | |
| 2009/0192591 A1 | 7/2009 | Ryan et al. | |
| 2009/0198316 A1 | 8/2009 | Laske et al. | |
| 2009/0216310 A1 | 8/2009 | Straubinger et al. | |
| 2009/0216312 A1 | 8/2009 | Straubinger et al. | |
| 2009/0216313 A1 | 8/2009 | Straubinger et al. | |
| 2009/0240264 A1 | 9/2009 | Tuval et al. | |
| 2009/0240320 A1 | 9/2009 | Tuval | |
| 2009/0287299 A1 | 11/2009 | Tabor et al. | |
| 2009/0292350 A1* | 11/2009 | Eberhardt et al. | 623/1.16 |
| 2010/0011564 A1 | 1/2010 | Millwee et al. | |
| 2010/0018447 A1 | 1/2010 | Holecek et al. | |
| 2010/0023120 A1 | 1/2010 | Holecek et al. | |
| 2010/0036484 A1 | 2/2010 | Hariton et al. | |
| 2010/0094411 A1 | 4/2010 | Tuval et al. | |
| 2010/0100167 A1 | 4/2010 | Bortlein et al. | |
| 2010/0131054 A1 | 5/2010 | Tuval et al. | |
| 2010/0137979 A1* | 6/2010 | Tuval et al. | 623/2.11 |
| 2011/0276128 A1* | 11/2011 | Cao et al. | 623/2.11 |
| 2012/0203335 A1* | 8/2012 | Vesely et al. | 623/2.18 |

FOREIGN PATENT DOCUMENTS

| | | |
|---|---|---|
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 48 814 | 9/2000 |
| DE | 10 49 815 | 4/2002 |
| DE | 100 49 812 | 4/2002 |
| DE | 100 49 813 | 4/2002 |
| EP | 0103546 | 3/1984 |
| EP | 0597967 | 12/1994 |
| EP | 0850607 | 7/1998 |
| EP | 1057459 A1 | 6/2000 |
| EP | 1057460 A1 | 6/2000 |
| EP | 1088529 | 4/2001 |
| EP | 1255510 | 11/2002 |
| EP | 0937439 B1 | 9/2003 |
| EP | 1340473 | 9/2003 |
| EP | 0819013 | 6/2004 |
| FR | 2788217 | 12/1999 |
| GB | 2056023 | 3/1981 |
| GB | 2433700 | 12/2007 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |
| WO | 2005/027790 | 3/2005 |
| WO | 2005/046528 | 5/2005 |
| WO | 2008/047354 | 4/2008 |
| WO | 2008/079962 | 7/2008 |
| WO | 2008/100599 | 8/2008 |
| WO | 2008/150529 | 12/2008 |
| WO | 2009/002548 | 12/2008 |
| WO | 2009/029199 | 3/2009 |
| WO | 2009/042196 | 4/2009 |

(56) References Cited

FOREIGN PATENT DOCUMENTS

| | | |
|---|---|---|
| WO | 2009/045338 | 4/2009 |
| WO | 2009/061389 | 5/2009 |
| WO | 2009/091509 | 7/2009 |

OTHER PUBLICATIONS

U.S. Appl. No. 12/711,289, filed Feb. 24, 2010.
Andersen, H.R. et al, "Transluminal implantation of artificial heart valves. Description of a new expandable aortic valve and initial results with implantation by catheter technique in closed chest pigs," Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Steps Toward Percutaneous Aortic Valve Replacement," Circulation (United States), Feb. 12, 2002, pp. 775-758.
Boudjemline, et al, "The Percutaneous Implantable Heart Valve," Progress in Pediatric Cardiology (Ireland), 2001, pp. 89-93.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Lutter, et al, "Percutaneous Aortic Valve Replacement: An Experimental Study. 1. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pasupati et al., "Transcatheter Aortic Valve Implantation Complicated by Acute Structural Valve Failure Requiring Immediate Valve in Valve Implantation," Heart, Lung and Circulation 2010; doi:10.1016/j.hlc.2010.05.006.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Webb, et al., "Percutaneous Aortic Valve Implantation Retrograde from the Femoral Artery," Circulation (2006), 113;842-850.
Expert report of Dr. Nigel Buller, dated Jan. 12, 2009, Edwards' United Kingdom action for invalidity, Claim No. HC 08C00934 (83 pages).
Expert report of Dr. Nigel Buller, non-confidential annex—infringement, dated Jan. 12, 2009, Edwards' United Kingdom action for invalidity, Claim No. HC 08C00934 (12 pages).
Expert report of Dr. Rodolfo Quijano, dated Jan. 9, 2009, Edwards' *LifeSciences v. Cook Biotech Incorporated*, United Kingdom action for invalidity, Claim No. HC 08C00934 (18 pages).
First Expert report of Prof. David Williams, dated Jan. 12, 2009, Edwards' United Kingdom action for invalidity, Claim No. HC 08C00934 (41 pages).
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.

\* cited by examiner

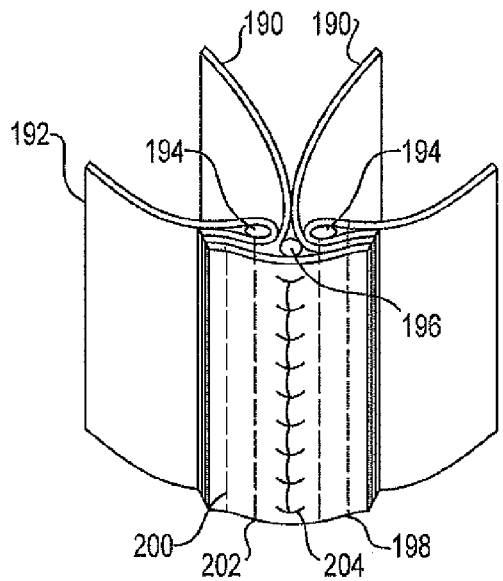
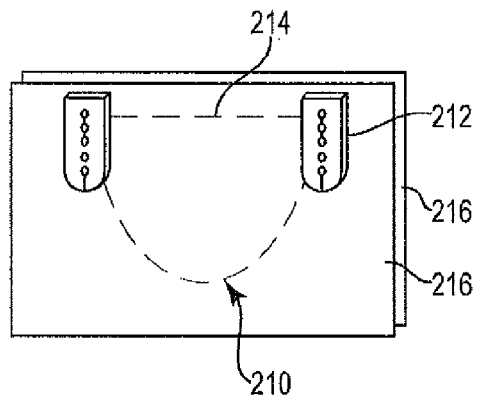
Fig. 22
Fig. 23
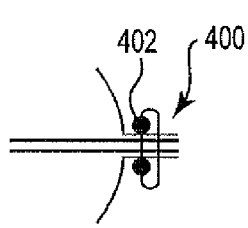 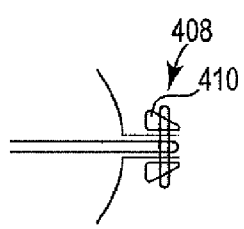 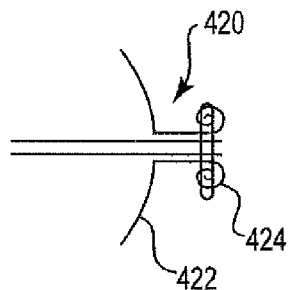
Fig. 24    Fig. 25    Fig. 26
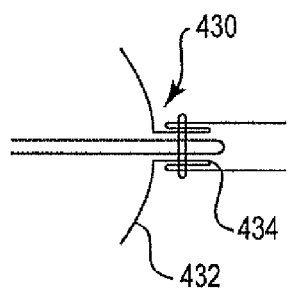
Fig. 27

TISSUE ATTACHMENT DEVICES AND METHODS FOR PROSTHETIC HEART VALVES

CROSS-REFERENCE TO RELATED APPLICATION

The present application claims priority to U.S. Provisional Application Nos. 61/125,203, filed Apr. 23, 2008, and titled "Tissue Attachment Devices and Methods for Prosthetic Heart Valves" the entire contents of which is incorporated herein by reference in its entirety.

TECHNICAL FIELD

The present invention relates generally to treatment of cardiac heart disease. More particularly, the present invention relates to implantable valve prostheses for implantation into the cardiac system.

BACKGROUND

All four of the valves in the heart are passive structures in that they do not themselves expend any energy and do not perform any active contractile function. They consist of moveable "leaflets" that open and close in response to differential pressures on either side of the valve. The problems that can develop with valves can generally be classified into two categories: (1) stenosis, in which a valve does not open properly, and (2) insufficiency (also called regurgitation), in which a valve does not close properly. Stenosis and insufficiency may occur concomitantly in the same valve or in different valves. Both of these abnormalities increase the workload placed on the heart. The severity of this increased stress on the heart and the patient, and the heart's ability to adapt to it, determine the treatment options that can be pursued. In some cases, medication can be sufficient to treat the patient, which is the preferred alternative; however, in many cases defective valves have to be repaired or completely replaced in order for the patient to live a normal life.

The two general categories of valves that are available for implantation into the cardiac system are mechanical valves and bioprosthetic or tissue valves. Mechanical valves have been used for many years and encompass a wide variety of designs that accommodate the blood flow requirements of the particular location where they will be implanted. Although the materials and design features of these valves are continuously being improved, they do increase the risk of clotting in the blood stream, which can lead to a heart attack or stroke. Thus, mechanical valve recipients must take anti-coagulant drugs for life to lessen the potential for blood clot formation. Further, mechanical valves can sometimes suffer from structural problems that may force the patient to have additional surgeries for further valve replacement.

Bioprosthetic valves, which are also referred to as prosthetic valves, generally include both human tissue valves and animal tissue valves. The designs of these bioprosthetic valves are typically relatively similar to the design of the natural valves of the patient and advantageously do not require the use of long-term anti-coagulant drugs. Human tissue valves are typically not available in large quantities, however, since they must be removed from deceased persons who have elected organ donation. On the other hand, due to the large numbers of animals routinely processed at meat processing facilities, for example, animal tissue valves are more widely available for the patients who require valve replacement. The most common types of animal tissue valves used include porcine aortic valves, and bovine and porcine pericardial valves, some of which are incorporated with some type of a stent before implantation in a patient. In the case of pericardial valves, the use of pericardial material to design and make the heart valves provides a much larger range of design options than is available when using only harvested valves.

In order to incorporate a tissue valve with a stent or other type of frame, a number of different techniques and methods have been used, such as clamping, tying, gluing, or stitching, for example. However, many of the techniques used for this purpose generally produce a stented valve that has concentrated stresses at the points where the leaflets are attached to the stent frame. That is, because the stents are relatively rigid as compared to the flexible material from which the leaflets of the tissue valve are made, the repetitive flexing motion of the leaflets can create stress concentrations at the points where the tissue valve is attached to the stent. These stress concentrations can eventually lead to tearing of the tissue, valve leakage, and/or failure of the heart valve. The attachment points can also be sites for abrasion of the tissue that can lead to tearing of the tissue. Thus, there is a continued need to be able to provide methods and devices for a durable attachment between a tissue valve and a stent and/or to distribute the stresses away from the attachment and seam areas and provide for nonabrasive contact surfaces for bioprosthetic heart valve leaflets.

SUMMARY

The present invention is directed to a prosthetic cardiac valve and methods of making such a valve. In particular, embodiments of the invention are directed to protection of seams that are formed by the attachment of pieces of tissue material when making a tubular valve.

In one aspect of the invention a multi-leaflet valve is provided, which includes at least two leaflets made from pericardial material, for example, an outer tube, and a seam protector for each seam. Each seam protector is positioned to be in contact with a portion of the outer tube, with tube portions and leaflet ends being positioned between adjacent seam protection pieces. The seam protectors provide a lower stress surface about which the leaflets can bend or flex during their opening and closing. The seam protectors may be configured in a number of different ways, including an enlarged end portion with an extending straight surface, an inverted U-shaped structure, a sinusoidal-shaped structure, and the like. The valve can further be provided with a seam cover or protector that is stitched onto the seam allowance of the layers of one or more of the seams. The seams can be provided with one or more inserts to fill spaces between adjacent tissue layers and create tension in certain material sheets, thereby providing a relatively soft hinging surface for the leaflets.

In one aspect of the invention, seam protection is provided by configuring a free end of tube material into a roll or coil at the seam area. In another aspect of the invention, a strip of material can be provided for seam support and to provide an element about which leaflets can bend.

In another aspect of the invention, a sheet of pericardium material can be cut or otherwise made into a disc of material from which a hole is cut in its central area. The inner hole can be attached to a stent frame and a plate or other fixture can be used to form the leaflet shapes.

BRIEF DESCRIPTION OF THE DRAWINGS

The present invention will be further explained with reference to the appended Figures, wherein like structure is referred to by like numerals throughout the several views, and wherein:

FIGS. 17a through 21b are schematic top views of seam protectors in pairs, where each pair of Figures includes the seam protector in its operational position and a mold configuration for making that seam protector;

FIG. 22 is a perspective view of a seam construction that includes the use of a back plate and support structures;

FIG. 23 is a front view of material used in forming a leaflet and including two support inserts;

FIGS. 24-29 are schematic side views of seam configurations of valves that are constructed with at least one element in addition to the tissue layers about which leaflets of the valve can flex;

DETAILED DESCRIPTION

Pericardial valves of the invention can be used for replacement of pulmonary valves, aortic valves, mitral valves, or tricuspid valves, in accordance with the methods and valve constructions of the invention described herein. Alternatively, the valves of the invention can be used to replace a failed bioprosthesis, such as in the area of an aortic valve or mitral valve, for example. The shape, size, and configuration of the outer tubular portion of the pericardial valve can specifically be designed and chosen for the type of valve that is being produced. The valves of the invention can include stented or stentless valves, but in either case, the valves are preferably compressible to a reduced diameter during the implantation process, such as for transcatheter implantation, and can be capable of being expanded to a larger diameter once they are in their desired implantation location. The valve assemblies can be used as a surgical sutureless or apical implant, and can be utilized in percutaneous replacement of cardiac valves, for example. One exemplary method for assembling a stented valve of the invention generally includes the manufacture and preparation of a valve segment, then a subsequent mounting or attachment of the prepared valve segment to a stent, which is described in further detail below.

Figure 1:
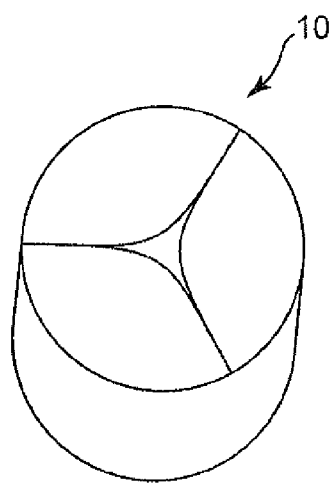
FIG. 1 is a schematic perspective view of a pericardial tri-leaflet valve of the invention.

Referring now to the Figures, wherein the components are labeled with like numerals throughout the several Figures, and initially to FIG. 1, a standard pericardial valve assembly 10 is illustrated, with its seams being located generally at the intersection line of adjacent leaflets. For the valve assembly 10, along with various embodiments of the invention described herein, at least one relatively flat sheet of pericardium material is used in their construction, which may be obtained, for example, from a swine. It is understood that other donor species may alternatively be used, or that the material used is not a pericardium material but instead is a different type of tissue or material, such as a polymer or bio-engineered film. The pericardium material may be at least partially fixed or cross-linked with a buffered gluteraldehyde solution or other solution at some point during the assembly process, in order to make the material easier for an operator to handle and manipulate. In one specific example, a piece of porcine pericardium is obtained, which is rinsed for approximately 10 minutes in a buffered gluteraldehyde solution to partially cross-link the material. U.S. Pat. No. 4,976,733 (Girardot), titled "Prevention of Prosthesis Calcification", describes a variety of additional exemplary methods of treating pericardium material that may be useful with the systems and methods of the present invention, along with methods for retarding or preventing the calcification of a prosthesis implanted in a mammal. However, such treatments to the material are optional and may be different depending on operator preference, the material chosen, and the like.

The piece of pericardium can then be cut to a predetermined shape and size to make the valve walls and leaflets of the valve assemblies of the invention, as will be described in detail relative to a number of embodiments of the invention. If the material is thicker than desired, the thickness can be reduced using a number of methods for effectively removing some of the thickness of the pericardium material without sacrificing an undesirable amount of the strength of the material.

Figure 2:
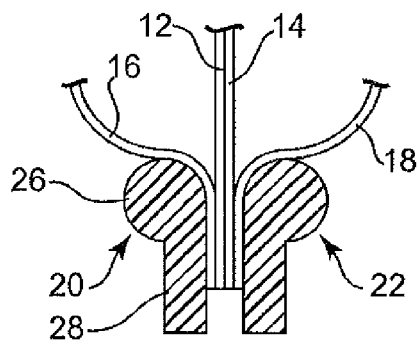
FIG. 2 is a cross-sectional top view of one seam of the pericardial valve of FIG. 1, including one aspect of a seam protection configuration.
Figure 3:
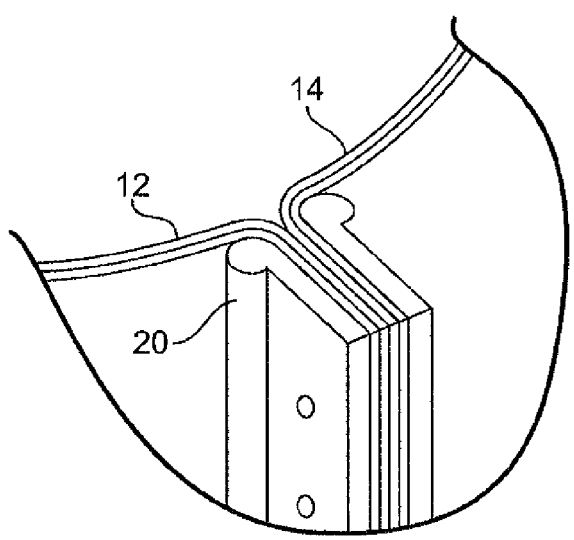
FIG. 3 is a perspective view of the seam of FIG. 2.
Figure 4:
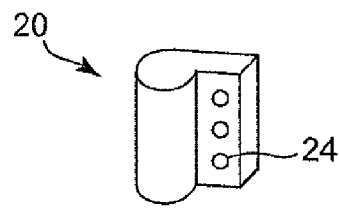
FIG. 4 is an isometric view of a seam protection fixture of the type used in FIGS. 1-3.

Referring to FIGS. 2-4, a seam of a valve is shown, which can be part of a bi-leaflet or tri-leaflet valve including two or three seams, respectively, attaching adjacent leaflets to each other and to an outside tube. The illustrated seam includes an end portion of a first leaflet 12, an end portion of a second leaflet 14, a first outer tube portion 16 that is adjacent to the first leaflet 12, and a second outer tube portion 18 that is adjacent to the second leaflet 14. As shown, the leaflets 12, 14 are positioned adjacent to each other and in between tube portions 16, 18 to create a stacked configuration at the seam. It is noted that the opposite sides or ends of each of the leaflet pieces would be attached at seams that are spaced from each other in order to create a multi-leaflet structure.

The seam protector comprises a first side piece 20 positioned to be in contact with the first outer tube portion 16 and a second side piece 22 (which is optionally configured to mirror the first side piece 20) positioned to be in contact with the second outer tube portion 18. The side pieces 20, 22 may be molded out of silicone, reinforced silicone, or plastic, for example, and are at least slightly more rigid than the leaflet and outer tube materials of the valve. As shown, each of the side pieces 20, 22 includes an enlarged end portion 26 from which a straight or flat portion 28 extends. The relative sizes and shapes shown for the enlarged end 26 and straight portions 28 of the side pieces 20, 22 are exemplary and can be different from that shown in the figures. In any case, the enlarged end portion 26 of each of the side pieces 20, 22 can be relatively cylindrical in shape and can provide a relatively gentle transition area for the outer tube portions. In this way, the stress concentrations in this area can be reduced. In addition, the enlarged end portion 26 provides a smooth surface to minimize abrasion where the leaflets open and close. Further, side pieces 28 can include multiple sewing holes 24, as shown in FIG. 4. Because these sewing holes 24 provide the locations through which sutures or other material can be inserted for attaching the layers of material to each other and to the side pieces 20, 22 of the seam protector, the positioning of these holes 24 (e.g., their distance from the enlarged end portion 26) can advantageously determine how far the stitching is spaced from the area about which the leaflets open and close. For example, in order to move the sewing line of the seam farther from the outer tubular wall of the valve assembly, the distance from the sewing holes 24 to the enlarged end portion of each side piece can be increased.

In order to assemble pericardial pieces at each of the seams of a tri-leaflet valve, three pieces of tissue are provided for the leaflets, each of which will be stitched outside of the stitch line that would normally be used. This stitching will position the seams away from the point or line along which the leaflets open and close. It is also contemplated to tack certain pieces of the pericardium that will be part of the structure to portions of a seam protector prior to placing all of the pieces in contact with each other. It is further contemplated that a clamp can be used to hold the pieces together during and/or after the stitching is complete.

Three similar or identical seam arrangements can be used to form a tubular structure of the type referred to as a tri-leaflet valve, or the seams can be configured differently from each other. In any case, seam protectors are preferably provided at each of the three seam areas. The valve assembly can then be attached to a compressible stent or other compressible structure for percutaneous or surgical delivery to the heart of a patient, for example.

Figure 5:
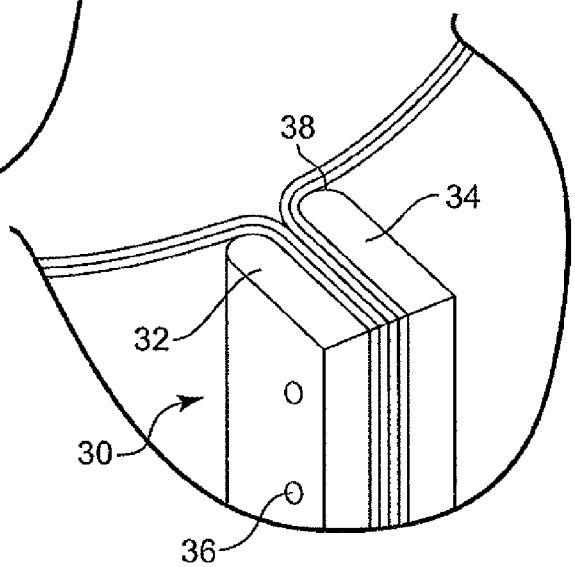
FIG. 5 is a perspective view of another seam protection configuration adjacent to a seam of a pericardial valve.

FIG. 5 illustrates another embodiment of a seam protector 30, which includes a first side piece 32 and a second side piece 34. Seam protector 30 also includes multiple sewing holes 36 that can again be spaced at a distance from the area about which the leaflets open and close in order to provide a stitch line that is not located at the area of the highest stress concentration for the leaflets. Side pieces 32, 34 have a generally rectangular shape with a curved distal edge 38 that is positioned against the outer layer of the tubular structure of the valve. As with other seam protectors described and shown herein, the curved or rounded edges 38 are intended to create a smooth transitional region around which tissue can bend, which is located at some distance from the seam in order to prevent tearing at the stitch line.

Figure 6:
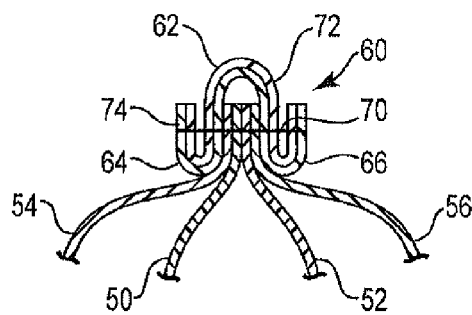
FIGS. 6-8 are cross-sectional views of different seam protection features attached to seams of a valve.

FIG. 6 illustrates another seam protection embodiment of the invention, which is used at a seam of a valve where first and second leaflets 50, 52 are attached to outer tube portions 54, 56 in a manner similar to that described above. This area further includes a seam protector 60 that is shown as having an inverted U-shaped portion 62 that covers the raw edges of the leaflets 50, 52 and tube portions 54, 56. The seam protector 60 further includes U-shaped portions 64, 66 that extend from opposite ends of the inverted U-shaped portion 62. All of these layers of material can then be stitched to each other, in a location that is spaced from the outer tubular wall, such as is shown by stitch 70. The bottom of the U-shaped portions 64, 66 are spaced from the stitch line and positioned to provide a curved surface around which the tissue can bend. The seam protector 60 can be a single or multiple layer structure. For one exemplary embodiment of a dual layer structure, a first layer 72 can be Dacron, fabric, or a silicone adhesive layer, and a second layer 74 can be a tissue material, such as a pericardial tissue, although a wide variety of biocompatible materials can be used. The layers 72, 74 can be attached to each other in a variety of ways, such as by sewing, ultrasonically welding, laser welding, or adhering the layers to each other with tissue glue. The first layer 72 can be provided with a large enough thickness so that the rounded edges created at the bottom of the portions 64, 66 provide a sufficiently large radius about which the tissue can bend.

Figure 7:
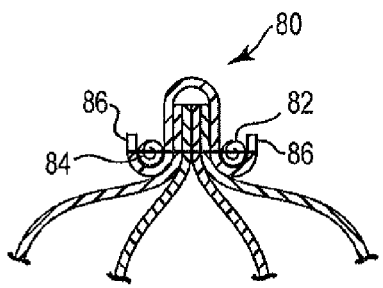

FIG. 7 is another exemplary seam protection embodiment that is similar to that shown in FIG. 6; however, a seam protector 80 of FIG. 7 further includes a structure or member 82 positioned within the open area of one or both of its U-shaped portions 86. The structure 82 provides additional structural integrity to the area about which the tissue can bend. The structure 82 may be made of a wide variety of materials, such as a piece of tissue that is rolled to a desired diameter, a fabric roll or piece of material, a silicone piece, or some type of wire or tubular piece, for example. The shape of the structure 82 may be round, elliptical, or the like, and preferably does not provide sharp edges that contact the tissue. This seam protector 80 is shown as having a single layer, such as a tissue layer, since the structure 82 is intended to form the rounded area about which the tissue can bend and thus can be provided with a desired size and shape for the bend region. Alternatively, the seam protector 80 can have a multiple-layer construction, although the combined size of the material thickness along with the size of the structures 82 should be considered to arrive at a desired overall radius for this portion of the seam protector 80. All of these layers of material can then be stitched to each other, in a location that is spaced from the outer tubular wall, such as is shown by stitch 84.

Figure 8:
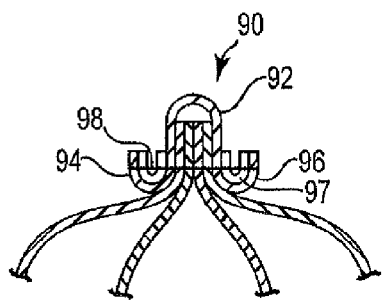

FIG. 8 is another exemplary seam protection embodiment that is similar to that shown in both FIGS. 6 and 7 in that seam protector 90 includes an inverted U-shaped portion 92 from which U-shaped structures 94, 96 extend to create a sinusoidal shaped structure. In this embodiment, an additional layer of material 97, which can be tissue or fabric, for example, is inserted into the open area of the U-shaped structures 94, 96 to provide additional structural integrity to the area about which the tissue can bend. All of these layers of material can then be stitched to each other, in a location that is spaced from the outer tubular wall, such as is shown by stitch 98.

Figure 9:
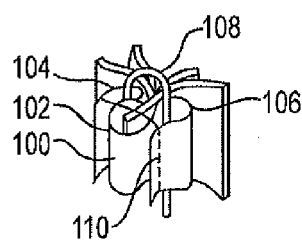
FIG. 9 is a perspective view of a seam protection feature with a seam of a valve.

FIG. 9 is a perspective view of another seam protection embodiment that includes a seam protector 100 having a U-shaped portion 102 from which inverted U-shaped structures 104, 106 extend. In this embodiment, a flexible tube or other structure 108 is formed or curved into a U-shaped configuration and positioned in such a way that each of its ends extends into the open area of the structures 104, 106. The structure 108 is shown as having a generally circular cross-section, although a different shape for the structure 108 can be chosen, where the shape and size of the structure 108 will help to provide the shape about which the tissue of the valve assembly will bend. The material layers and seam protection components are attached to each other at a seam as shown by the exemplary stitching 110, which is spaced at a distance from the point where the material layers are under the greatest stress during operation of the valve.

Figure 10:
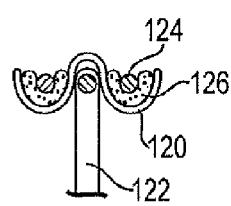
FIG. 10 is a cross-sectional side view of a seam protection feature incorporating a fabric coated with silicone and cured into a sinusoidal shape.

FIG. 10 is a cross-sectional view of a seam protection feature incorporating a fabric or cloth material 120 that at least can be partially coated with silicone and cured into a sinusoidal shape. A wire 124 can be provided in the open area or areas of the sinusoidal shaped cloth piece. A quantity of silicone or other material 126 can be inserted into at least a portion of the open space(s) of the material 120 to at least partially surround the wire 124. A portion of a leaflet 122 is also shown relative to this seam protection feature.

Figure 11:
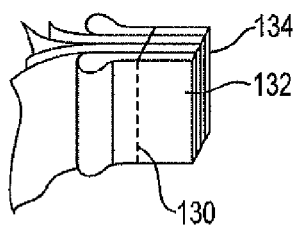
FIGS. 11-12 are perspective views of seam protection features attached to a seam of a valve.
Figure 12:
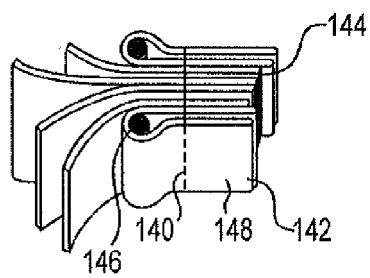

FIGS. 11 and 12 illustrate multiple material or tissue layers at the seam of a valve assembly of the types described above, for example. In these embodiments, rather than covering the seam from the back, which may be difficult to secure due to the difficulty in precise placement of the tissue edges, the pieces can instead be secured or sewn separately and trimmed. In particular, the seam of FIG. 11 includes first and second seam protection side pieces (of the type generally shown in FIG. 1) on opposite sides of the multiple tissue layers of the valve tube and leaflets, along with a stitching line 130 that is spaced between the enlarged end of the first and second side pieces and the exposed or raw edges of tissue 134. The portion 132 of tissue extending between the stitching line 130 and the raw tissue edges 134 can be trimmed after sewing, if desired. Similarly, the portion of tissue 142 of FIG. 12 extending between the stitching line 140 and the raw edges of tissue 144 can be trimmed after sewing, if desired. In this embodiment, a piece of material or member 146 is wrapped with a tissue, fabric, or other sheet material 148 and attached on both sides of the seam to provide the surface about which the layers of tissue in the seam can bend. In order to join tissue prior to covering for seam protection, a laser weld can be used. Alternatively, the tissue layers can be "tack welded" together or secured to each other in some other manner.

Figure 46:
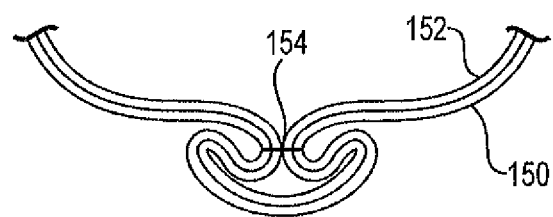
FIGS. 46 and 47 are top views of a seam protection feature provided by the material that forms the leaflet and the valve wall.
Figure 47:
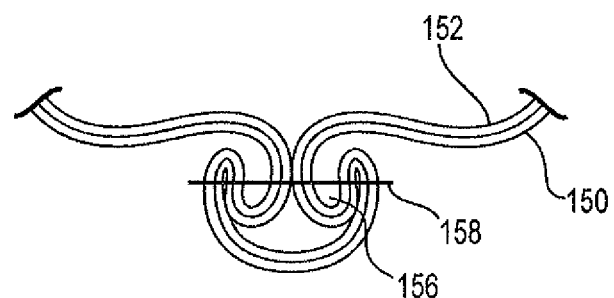

FIGS. 46 and 47 illustrate a tube layer of material 150 and a layer of leaflet material 152 that have been stitched and configured in such a way that the tissue layers 150, 152 themselves create the seam protection. In particular, the two tissue layers are folded about a seam line and sewn along the stitch line 154 shown in FIG. 46. Padding or other material can be inserted in the area indicated as reference numeral 156 on one or both sides of the seam in FIG. 50 to provide additional seam protection. As shown in FIG. 47, a stitch 158 can be run through several of the layers of material to secure any padding or material in the area or areas 156 and to also secure the material layers to each other.

Figure 13:
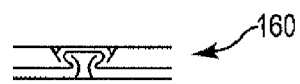
FIG. 13 is a schematic view of a seam attachment configuration for a valve of the invention.

FIG. 13 illustrates one embodiment of a dovetail type of seam 160 for securing tissue and providing a non-abrasive hinging edge about which the tissue of the leaflets can flex. As shown in this embodiment, layers of tissue are provided with features that are engageable with each other in a locking manner.

Figure 14:
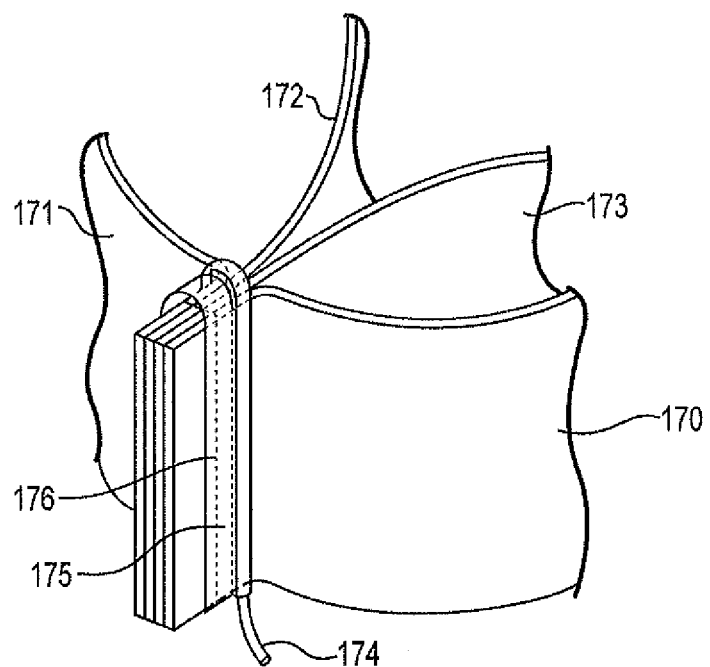
FIGS. 14 and 15 are perspective views of additional seam protection embodiments of a valve.
Figure 15:
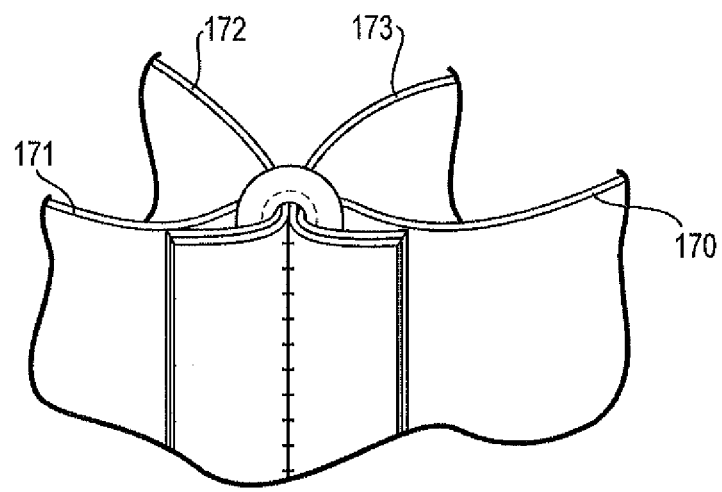

FIG. 14 is another embodiment of a pericardial valve that includes outer tube layers 170, 171 and leaflets 172, 173, where this figure shows just one seam of a multiple leaflet valve. This embodiment further includes a wire 174 covered with a material layer 175 as shown in the Figure, which can be cloth or pericardium, for example. This layer 175 may be sewn along stitch line 176, for example, prior to it being attached to the tissue layers, where the wire can be bent and the wire ends can be cut or attached to a stent. The material layer 175 is sewn in the general area about which the leaflets will flex to enclose the wire and secure it to the valve. The layers of material may be stitched along stitch line 176, for example. The sewing area is chosen so that the stitches secure the covering of the wire (e.g., cloth or pericardium) to the seam allowance layers of the leaflets and outer tube layers 170, 171. FIG. 15 illustrates the seam allowance opened and folded back toward the outer tube layers 170, 171 of the valve.

Figure 16:
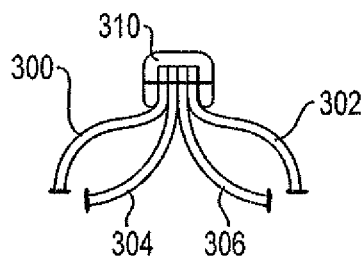
FIG. 16 is a cross-sectional view of a seam including an attached seam protector.

FIG. 16 illustrates another embodiment of a seam of a valve assembly of the type described above. In particular, this embodiment illustrates outer tube portions 300, 302 and ends of leaflets 304, 306 positioned relative to each other in generally the manner described above. The embodiment further includes a seam protector or cover 310 that is stitched onto the seam allowance of the layers of the seam. The seam cover 310 can be semi-rigid to help protect the seam from wear. One exemplary way of manufacturing such a seam cover 310 is to mold it into a desired shape from silicone, Teflon, or the like.

Figures 17A, 17B:
Figures 18A, 18B:
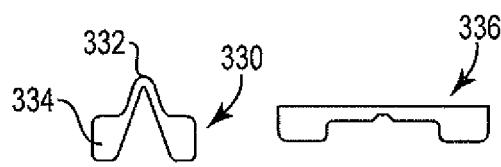
Figures 19A, 19B:
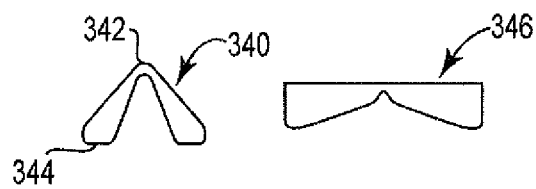
Figures 20A, 20B:
Figures 21A, 21B:
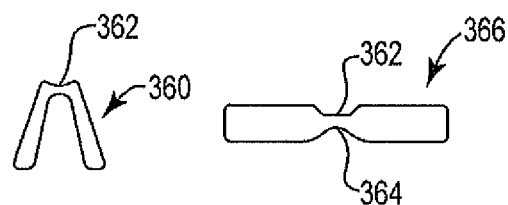

A variety of exemplary shapes for seam covers and molds for making these seam covers are shown in FIGS. 17a-21b. In particular, FIG. 17a illustrates a seam cover 320 that has a generally uniform thickness and FIG. 17b shows a cross section of a mold 322 for making the seam cover 17a, which includes a notch 324 to provide easier folding of the seam cover. FIG. 18a shows another seam cover 330 that is relatively thin at the top area 332 to improve the ease of stitching it to the valve, and is thicker in the bottom area 334 to provide additional rigidity to the seam cover. The length of the thick portion 334 can vary depending on the desired distance of the seam from the inner portion of the heart valve. FIG. 18b shows a cross section of a mold 336 for making the seam cover 330 illustrated in FIG. 18a. Another seam cover 340 is illustrated in FIG. 19a, which is relatively thin at the top or bend area 342 to provide ease in stitching it to the valve, and tapers to be thicker toward the free edges 344 to provide additional rigidity to the seam cover 340. FIG. 19b shows a cross section of a mold 346 for making the seam cover 340 illustrated in FIG. 19a. FIG. 20a illustrates another seam cover 350 that is relatively thin at the top area 352 and has knob portions 354 at its free edges. FIG. 20b shows a cross section of a mold 356 for making the seam cover 350 illustrated in FIG. 20a. Finally, FIG. 21a is a cross-sectional view of another seam cover 360 that includes notches 362, 364 on opposite sides, where the notch 362 on the outside is to provide ease in folding the seam cover 360 and the notch 364 on the inside is provided to accommodate the thickness of the tissue. FIG. 21b shows a cross-sectional view of a mold 366 for making the seam cover 360 illustrated in FIG. 21a.

When stitching any of the seam covers described above to the seam of a valve, it may be desirable to use a template; however, in order to use a template for a seam cover (which may be made of silicone or the like) while also minimizing the bulkiness of the seam, enough surface area should be provided for clamping the materials onto the template. That is, the width of the seam cover can be increased to be at least slightly larger than necessary, and the extra material can be trimmed away after the seam has been stitched.

FIG. 22 shows another seam configuration of a heart valve in accordance with the invention, which includes leaflets 190 and an outer layer 192 of tube on each side of the seam. The seam further includes a relatively rigid insert 194 on each side of the seam. The inserts 194 can be polymer strips having a series of stitching holes, for example, or may have another configuration. The seam further includes another insert 196 that can be relatively soft compared to the more rigid inserts 194 and can be made out of a tissue or fabric roll, rope, or braid, for example. However, the relative rigidity of the inserts can vary widely, depending on the desired characteristics for the valve. Insert 196 can be designed to fill the space between the tissue layers and create tension in a back panel 198 by pulling the inserts 194 toward one another and capturing the leaflets against a relatively soft hinging surface. The back panel 198 can be a relatively flexible sheet of material such as pericardium, fabric, or a synthetic material. The back panel 198 can be attached with a blanket or whip stitch, for example, as shown by reference number 204. This stitching can extend through the back panel 198 and through the insert 196 in order to remove slack in the back panel 198, create tension, and pull the inserts 194 toward each other. Optional sewing along one or more stitch lines 200 on both sides of the seam can extend through all the layers to encase the inserts 194. Sewing along optional stitch lines 202 on both sides of the seam will extend only through the inserts 194, the back panel 198, and the seam allowance layers. The valve can be attached to a stent at this seam by sewing through the back panel 198, which can provide compliance between the relatively rigid stent and the relatively flexible valve. Alternatively, the back panel 198 can be eliminated from the construction and any rigid inserts 194 can be whip or blanket stitched together. The use of these inserts 194 encased by the outer tube layer 192, when secured end to end as shown, provide a nonabrasive hinging region for the leaflets of the seam. In addition, this seam configuration moves the leaflet hinge or pivot point away from the leaflet/stent or valve attachment point by pulling the leaflet/rigid insert seam toward the stent, away from the inside of the valve, and securing it in place by attaching the back panel to the leaflet and tube seam allowances and rigid inserts.

FIG. 23 illustrates two layers of pericardium 216 and two relatively rigid inserts 212 used in a seam construction. In particular, the layers 216 are sewn to each other along line 210 to create the margin of attachment of a leaflet. The free margin is cut along line 214, which is shown as a hidden line, since that cut would be through the bottom layer shown in the figure. The inserts 212 are sewn to the outside layer and in some embodiments are also sewn to the leaflet layer. At least one end of each of the inserts 212 is preferably rounded so that the transition between the margin of attachment stitches and the inserts 212 is smooth. The inserts 212 are positioned so that the margin of attachment stitches are generally tangential to the edge of the inserts. Three of these constructions can be used in making a tri-leaflet valve.

FIGS. 24-27 illustrate several exemplary seam constructions, some of which are similar to those discussed above and therefore can include the variations and features discussed above relative to seams for pericardial heart valve constructions. All of these seam constructions are provided as ways to reduce or eliminate exposure of the stitches to the inside of the valve and the blood stream, while minimizing the size of the seam. FIG. 24 shows a seam construction 400 that uses generally cylindrical pieces of material 402, such as rolled or folded pericardium, PTFE, silicone, or the like, which is stitched to the layers of tissue of the seam. The portion of each material piece closest to the valve is fairly rigid and may allow the leaflets to flex at the material piece rather than at the stitches. The size of the material pieces 402 should be as small as possible to minimize the size of the seam, but large enough to keep rigidity and allow the leaflets to flex around them. The material pieces 402 are also preferably flexible enough that they can be crimped down with the stent without compromising the security of the stitching.

FIG. 25 illustrates a variation 408 of the seam construction of FIG. 24. The construction of FIG. 25 includes material pieces 410 that are more triangular in shape to improve the flexibility at the flex point and prevent the seam from opening up to expose the sutures to the inside of the tube. FIG. 26 illustrates another exemplary seam construction 420 that includes rolling the free end of an outer tube material 422 on itself to make a coil of material 424 (e.g., pericardial tissue). When sewing the seam, the stitches can be positioned to penetrate through some or all of the layers of material of the coil 424. This construction 420 advantageously utilizes material that is already part of the valve construction and therefore does not require additional separate elements. In this embodiment, the length of the pieces of outer tube material 422 should be long enough to provide sufficient material to make the coil of material 424. FIG. 27 illustrates yet another seam construction 430 of a heart valve that includes folding a free edge of an outer tube material 432 on itself to create at least one loop of material 434 at the area about which the leaflets will flex. A wire or other material can be inserted into the loop of material nearest the outer tube layer 432 to give a more rounded shape to this portion. The free ends of the outer tube layer 432 can be trimmed to minimize the bulkiness of the seam, if desired.

Figure 28:
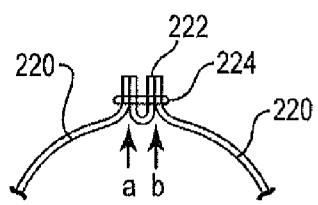
Figure 29:
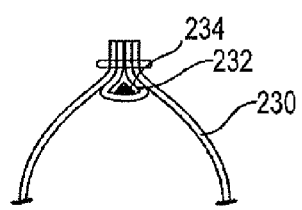

FIGS. 28 and 29 show two seam constructions that are particularly configured to minimize or eliminate exposure of the sutures to the inside of the valve. FIG. 28 shows leaflets 220 and a center loop or piece of material 222 (e.g., pericardial tissue) that are situated relative to each other so that the leaflets 220 can flex about the points "a" and "b". Because the center material 222 would not be flexing, there will not be a large gap at these points, thereby minimizing exposure of the inside of the valve to the seam. FIG. 29 illustrates a seam that is similar to that of FIG. 28, but also includes an additional piece of material 234 between the layers of a material loop 232. This material piece 234 is preferably designed to even better improve the quality of the seal between the material loop 232 and the leaflets 230 to minimize exposure of the inside of the valve to the seam.

Figures 30, 31:
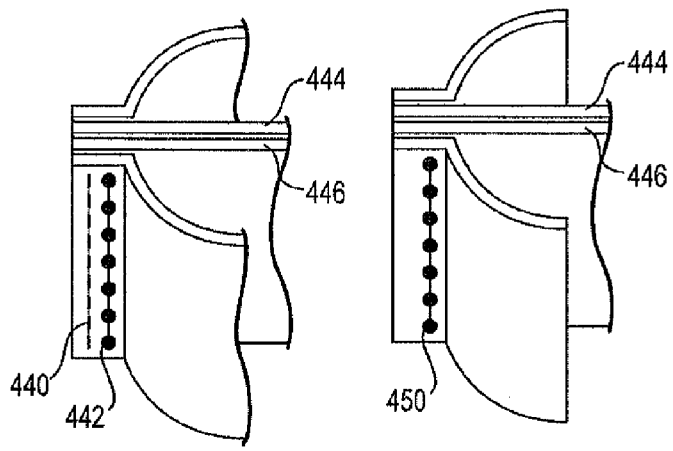
FIGS. 30 and 31 are perspective views of additional tissue seam constructions.
Figure 32:
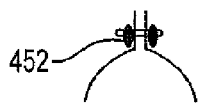
FIG. 32 is a schematic top view of a seam configuration that includes non-circular structures stitched into the seam.

Additional seam constructions are illustrated in FIGS. 30-32, which provide a strip for seam support and an element about which leaflets 444, 446 can bend. In particular, FIG. 30 shows a main seam 440 (indicated by dashed lines) and a strip of rigid "balls" 442 sewn into the construction at a line about which leaflets 444, 446 can flex. The spacing of these balls 442 from each other can be similar to that shown, or the balls 442 can be closer to or further from each other as compared to the figure. FIG. 31 shows a construction similar to that of FIG. 35. In this embodiment, the main seam and the rigid ball support strip 450 are on the same stitch line. With both of these embodiments of FIGS. 30 and 31, it can be advantageous for the balls to be very close to each other when the valve is in its expanded condition, but that the balls are further from each other when the valve is crimped or compressed due to the elongation of the valve. This is different from a solid strip, which can also be used in this area, in that the balls can move away from each other during compression, while a solid strip would need to stretch during a similar compression.

In the top schematic view of FIG. 32, one ball 452 of a strip is shown as being oblong in shape, where the strip can include a series of balls, and stitching extends through each of the oblong-shaped balls. The balls of these constructions can be plastic, metal, or another material and can be preformed, or the balls can be formed by placing fast-curing drops of material along the desired sewing line. The balls 452 may also have a different shape other than spherical, elliptical, and the like.

Figure 33:
FIG. 33 is a schematic top view of a seam configuration that includes a sewing strip.
Figure 34:
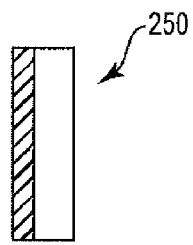
FIGS. 34 and 35 are front views of exemplary sewing strips that can be used in seam constructions for valves.
Figure 35:
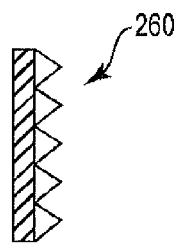
Figure 36:
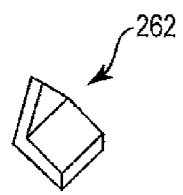
FIG. 36 is a perspective view of a shortened sewing strip of FIG. 35.

A variety of sewing strips can be used in combination with other features of the invention relative to seam construction, or the sewing strips that are shown and described herein relative to FIGS. 33-36 can be used alone or with other seam constructions. In any case, the sewing strips can be provided along a seam line for stitch and seam support and are preferably as small as possible to minimize bulk in the seam area, while still providing desired properties for the seam support. The sewing strips may include one strip that extends the entire height of the valve, or a series of strips may be used so that they can move relative to each other during elongation caused by stent crimping. One exemplary sewing strip shape is illustrated in FIG. 33 with the L-shaped strips 250, one of which is also shown in FIG. 34, positioned on opposite side of leaflets 252. Note that this embodiment does not include an outer tube, although these sewing strips can also be used with valve constructions that do include an outer tube. In order to also accommodate the diamond-shape of some stent struts, the sewing strip could instead be configured as shown in FIGS. 35 and 36 as strips 260, 262. In this configuration, triangular shaped extensions are designed to follow the strut pattern of the stent to which the valve will be attached. With any of the sewing strips, the material from which the sewing strip is made can be relatively flexible to allow for variations in the stent dimensions. Any of the sewing strips may be made of a silicone, rubber, another extruded polymer, pericardial material, and the like.

Figure 37:
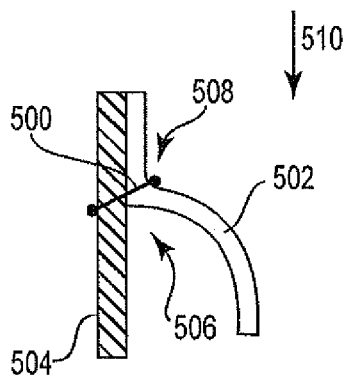
FIGS. 37-42 are cross-sectional side and perspective views of attachment configurations between leaflets and an outer tube, along with structures that are positioned to change stresses in the leaflet flexing areas.
Figure 38:
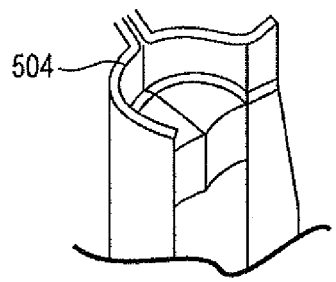
Figure 39:
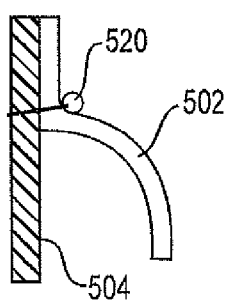
Figure 40:
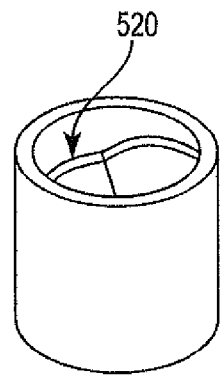
Figure 41:
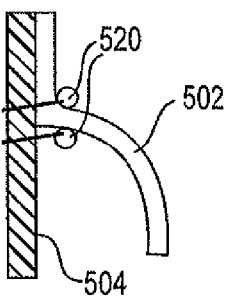
Figure 42:
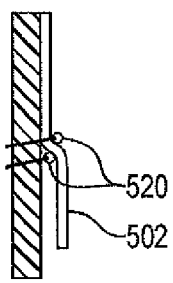

FIGS. 37-42 illustrate various configurations of placement of a roll or strip of material along the seam of a leaflet margin of attachment so that the leaflet flexes about the roll or strip of material rather than the high stress area of the suturing or sewing line. FIGS. 37 and 38 show a construction that does not include such a strip of material, but includes a suture 500 that attaches a leaflet 502 directly to a tube wall 504 such that as the leaflet 502 opens and closes, the tissue flexes directly about the suture 500 at the areas designated by reference numbers 506 and 508. A preferred direction for the inflow of blood is indicated by arrow 510. FIG. 39 adds a roll or strip of material 520 to the basic construction of FIG. 37, where this roll or strip of material 520 provides an element about which the leaflets 502 can flex. FIG. 40 shows a valve in a closed position with the roll of material 520 illustrated as being positioned on top of the leaflets. FIGS. 41 and 42 include two rolls or strips of material 520, with the strips of material 520 located on opposite sides of the leaflet 502 so that the leaflets 502 can flex about these strips of material 520.

Figure 43:
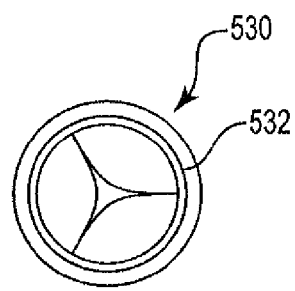
FIG. 43 is a schematic top view of a stented valve configuration including an additional cloth area in the construction.

FIG. 43 is a top view of a valve construction 530 that includes a layer of cloth 532 (e.g. cloth available under the trade designation "Dacron") between the stent and the valve tissue. The cloth layer could be sewn or otherwise attached to a stent, then the tissue tube could be sewn or attached to only the cloth layer. In this way, when the stent is crimped, the cloth layer can stretch with the stent and the tissue will either (a) not stretch, or (b) stretch less than if the cloth layer was not included in the construction. That is, the cloth layer can help to minimize the stresses on the tissue and keep it from needing to deform excessively when the stent is compressed and expanded.

Figure 44:
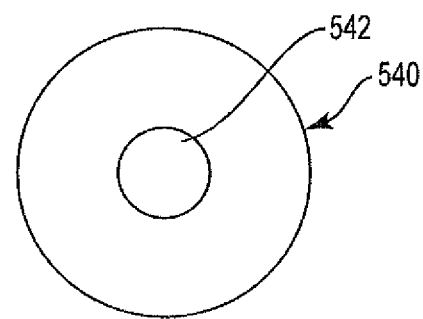
FIG. 44 is a top schematic view of a circular shaped disc of pericardial material that will be used in creating a valve.
Figure 45:
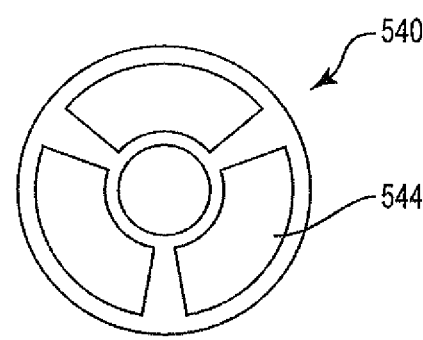
FIG. 45 is a schematic top view of the disc of FIG. 44 after a fixture has been used to form leaflet shapes from the pericardial material.

FIG. 44 is another alternate construction of a pericardial valve that starts with a sheet of pericardium from which a disc of material 540 is cut. A hole 542 is then cut in the center of the disc, where the size of the center hole is the same as the inner diameter of a selected valve size. This inner hole 542 is sewn or otherwise attached to the inflow side of a stent frame (not shown). A plate or other fixture can then be used to form the leaflet shapes 544 (see FIG. 45) by pressing the flat sheet of tissue between plates, then fixing the material in one of the manners described herein and/or in a manner commonly known in the art for fixing pericardial material. Alternatively, the leaflets 544 can be shaped after placing the material on a stent. In either case, the tissue in between the leaflet forms would then be pulled through slots of a stent form and attached on the outside of the stent.

In many of the embodiments described herein, the pericardial valve is prepared to include three leaflets, but may optionally have more or less than three leaflets, which can be formed by selecting the desired number of leaflet and outer tube components. The three leaflet embodiment can be used in areas of the heart that typically have a three leaflet valve, such as the pulmonary valve and aortic valve, although the three leaflet embodiment can also be used as a replacement for the two leaflet mitral valve. Alternatively, a two leaflet or single leaflet embodiment of the valve of the invention is contemplated, which can be used in areas of the heart that typically have a three leaflet valve, such as the pulmonary valve, for example. Certain considerations for blood flow will determine particular parameters of the valve used, as will be explained in further detail below.

The valve constructions of the invention may be used alone as a stentless valve, or the valve segments may be attached to a support structure such as a stent. The stent may be compressible for percutaneous delivery to the heart of a patient, for example. The stent used may take the form of a series of zig-zag ring structures and may be fabricated of platinum, stainless steel, or other biocompatible metal or polymer. The stent used may alternatively be fabricated using wire stock or may be produced by machining the stent from a metal tube, as is commonly employed in the manufacturing of stents. The number of wires, the positioning of such wires, and various other features of the stent chosen can vary considerably. Thus, the specifics of the stent can vary widely, such that many other known generally cylindrical stent configurations may be used within the scope of the invention. A series of zig-zag ring structures can be coupled longitudinally to one another to form a generally cylindrical-shaped structure, although it is understood that the structures can be arranged in an at least slightly oval or elliptical shape. Each ring structure can take the form of a series of adjacent generally straight sections, which each meet one another at one end at a curved or angled junction to form a "V" or "U" shaped structure.

Once a valve segment and stent are positioned relative to each other, the stent can be secured to the valve segment in a variety of ways. One procedure that can be used is to suture certain areas of the stent to the valve segment. The suture material may be provided as a monofilament or multifilament structure made of natural or synthetic materials (e.g., nylon or polypropylene), or may alternatively include an elongated metal or metal-composite thread or filament that is suitable for permanently securing the stent to the valve segment in accordance with the present invention. The number and location of suture points can vary, but should include an adequate number of connection points that are positioned in predetermined locations that prevent movement of the stent relative to the valve segment, particularly during the compression of the stent for percutaneous delivery and expansion of the stent for its deployment.

The valves or stented valves of the invention can be subjected to suitable chemical fixation and/or bioburden reduction treatments, which may vary considerably. Chemical fixation helps to preserve the tissue, render it inert, reduce the risk of host rejection, and/or the like. Chemical fixation may occur by submerging the valve in a suitable reagent for a period of about 3 hours under slight pressure and ambient temperature and then for 72 hours under ambient pressure and temperature. By way of example, a 0.2 weight percent gluteraldehyde solution at physiological pH and being phosphate buffered may be used for chemical fixation. The valve may then be stored in a suitable storage reagent (e.g., an aqueous solution containing 0.2% by weight gluteraldehyde) until subsequent use. Bioburden reduction may be carried out by submerging the tissue in a suitable reagent for a period of 48 to 72 hours at ambient temperature. By way of example, an aqueous solution containing 1% by weight gluteraldehyde and 20% by weight isopropyl alcohol at physiological pH and being phosphate-buffered may be used for bioburden reduction. This solution would be suitable for use as a packaging solution as well. A variety of fixation tines, concentrations, pH levels and chemicals can be used in accordance with the invention. After suitable treatments to the valve are complete and after appropriate rinsing of the valve, the device can be used for implantation into a human.

When valves of the invention are made into a stented valve, the stented valves may be used with a system for delivering the valve segment to the desired location within a patient. The delivery system may include, for example, an outer sheath overlying an inner balloon catheter, where the outer sheath includes an expanded distal portion, within which the stented valve is located. The stented valve can be compressed around a single or double balloon located on the inner catheter. A tapered tip mounted to the distal end of the inner catheter can ease the passage of the delivery system through the patient's vasculature. The system also may include some type of guidewire to guide the delivery system to its desired implant location. Another alternative delivery system that can be used, in particular, for stented valves having a self-expanding stent, includes a catheter that does not have balloons, but instead includes a sheath or other mechanism that maintains the self-expanding stent in its compressed condition until it is desired to allow it to expand. When such a self-expanding stent is properly positioned in the patient, the mechanism that keeps the stent compressed can be retracted or otherwise removed to allow for expansion of the stent against the vessel walls.

The delivery system and its use may be used where the stented valve can be expanded against a failed native or prosthetic valve. The delivery system can be advanced to the desired valve implant site using the guidewire, after which the sheath is moved proximally, exposing the valve and balloon mounted on inner catheter. The balloon is expanded, which thereby expands stented valve until it reaches a desired outer diameter where it contacts the wall of a heart vessel. The balloon is then deflated and the delivery system is withdrawn proximally.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A multi-leaflet heart valve defining a lumen, the heart valve comprising:
    a first leaflet having first and second sides;
    a second leaflet having first and second sides, wherein the first side of an end portion of the first leaflet is adjacent to the first side of an end portion of the second leaflet;
    a first outer tube layer having first and second sides, wherein the first side of an end portion of the first outer tube layer is adjacent to the second side of the end portion of the first leaflet;
    a second outer tube layer having first and second sides, wherein the first side of an end portion of the second outer tube is adjacent to the second side of the end portion of the second leaflet; and
    a first seam protector adjacent to and lying along at least a portion of the surface of the second side of the first outer tube layer;
    wherein the first seam protector comprises a first curved surface facing the lumen of the heart valve, the first curved surface being positioned along a line about which the first leaflet will flex;
    wherein the first seam protector comprises an enlarged cylindrical portion and an extending linear portion, wherein the cylindrical portion defines the first curved surface.

2. The valve of claim 1, further comprising a second seam protector;
    wherein the second seam protector is adjacent to the first seam protector;
    wherein the second seam protector is adjacent to and lying along at least a portion of the surface of the second side of the second outer tube layer; and
    wherein the second seam protector comprises a second curved surface facing the lumen of the heart valve, the second curved surface being positioned along a line about which the second leaflet will flex.

3. The valve of claim 2, wherein each of the first and second seam protectors comprises a first end, a second end, and multiple sewing holes, wherein the sewing holes are sized and spaced between the first and second ends of the seam protector at a predetermined distance from first and second flexure lines about which the first and second leaflets will open and close, respectively.

4. The valve of claim 1, further comprising a third leaflet, wherein the valve comprises three seams.

5. The valve of claim 1, wherein at least one of the first and second leaflets and the first and second outer tube layers comprise a sheet of pericardial material.

6. The valve of claim 1, wherein the first seam protector is at least slightly more rigid than each of the first and second leaflets and the first and second outer tube layers.

7. The valve of claim 6, wherein the first seam protector comprises at least one of silicone, reinforced silicone, and plastic.

8. The valve of claim 7, wherein each of the first and second leaflets and the first and second outer tube layers is formed from one of a sheet of pericardium material, a polymer film, and a bio-engineered film.

9. The valve of claim 1, further comprising:
    a third leaflet having first and second sides, wherein the first side of an end portion of the second leaflet is adjacent to the first side of an end portion of the third leaflet;
    a third outer tube layer having first and second sides, wherein the first side of an end portion of the third outer tube layer is adjacent to the second side of the end portion of the third leaflet; and
    a third seam protector adjacent to and lying along at least a portion of the surface of the second side of the second outer tube layer.

10. A prosthetic heart valve defining a lumen, the heart valve comprising:
- a first tissue layer having first and second sides;
- a second tissue layer having first and second sides, wherein the first side of the first tissue layer is adjacent to the first side of the second tissue layer to form a seam of the heart valve; and
- a first seam protector adjacent to and lying along at least a portion of the surface of the second side of the second tissue layer, the first seam protector comprising a first enlarged cylindrical portion and a first extending linear portion, wherein the first cylindrical portion defines a first curved surface facing the lumen of the heart valve and positioned along a line about which the second tissue layer flexes.

11. The heart valve of claim 10, further comprising a second seam protector, the first and second tissue layers being positioned between the first and second seam protectors.

12. The heart valve of claim 11, wherein the second seam protector comprises a second enlarged cylindrical portion and a second extending linear portion, wherein the second cylindrical portion defines a second curved surface facing the lumen of the heart valve.

13. The heart valve of claim 10, wherein the first seam protector comprises a first end, a second end, and multiple sewing holes, wherein the sewing holes are sized and spaced between the first and second ends of the first seam protector at a predetermined distance from a flexure line about which the second tissue layer will flex.

14. The heart valve of claim 10, wherein the first seam protector is at least slightly more rigid than each of the first and second tissue layers.

15. The heart valve of claim 14, wherein the first seam protector comprises at least one of silicone, reinforced silicone, and plastic.

16. The heart valve of claim 10, wherein each of the first and second tissue layers comprises pericardium.

* * * * *